(12) United States Patent
Ko et al.

(10) Patent No.: US 9,132,263 B2
(45) Date of Patent: Sep. 15, 2015

(54) FLEXIBLE ULTRASOUND ACTUATOR

(71) Applicant: INDUSTRIAL TECHNOLOGY RESEARCH INSTITUTE, Chutung, Hsinchu (TW)

(72) Inventors: Wen-Ching Ko, Kaohsiung (TW); Che-Yuan Sun, Hualien (TW); Chang-Yi Chen, Hsinchhu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 367 days.

(21) Appl. No.: 13/730,622

(22) Filed: Dec. 28, 2012

(65) Prior Publication Data

US 2014/0121588 A1   May 1, 2014

(30) Foreign Application Priority Data

Oct. 31, 2012  (TW) .............................. 101140281 A

(51) Int. Cl.
*H01L 41/09* (2006.01)
*A61M 37/00* (2006.01)
*B06B 1/06* (2006.01)
*A61B 8/00* (2006.01)

(52) U.S. Cl.
CPC .......... *A61M 37/0092* (2013.01); *B06B 1/0603* (2013.01); *B06B 1/0611* (2013.01); *A61B 8/4494* (2013.01)

(58) Field of Classification Search
CPC .............................. H04R 17/00; H04R 17/005
USPC .......... 310/311, 323.01–323.19, 323.21, 328, 310/331, 359, 371, 800
See application file for complete search history.

(56) References Cited

U.S. PATENT DOCUMENTS

| | | | | |
|---|---|---|---|---|
| 3,365,592 A | * | 1/1968 | Krautwald et al. | 310/331 |
| RE27,116 E | * | 4/1971 | Miller et al. | 310/359 |
| 5,656,882 A | * | 8/1997 | Lazarus et al. | 310/328 |
| 6,097,133 A | * | 8/2000 | Shimada et al. | 310/358 |
| 6,239,535 B1 | | 5/2001 | Toda et al. | |
| 6,279,810 B1 | | 8/2001 | Chan-Wong et al. | |
| 6,323,580 B1 | * | 11/2001 | Bernstein | 310/324 |
| 6,491,657 B2 | | 12/2002 | Rowe et al. | |
| 6,512,323 B2 | * | 1/2003 | Forck et al. | 310/332 |

(Continued)

FOREIGN PATENT DOCUMENTS

| | | | | |
|---|---|---|---|---|
| CN | 1610979 A | | 4/2005 | |
| DE | 10040994 A1 | * | 3/2002 | H04R 15/00 |

(Continued)

OTHER PUBLICATIONS

Liu et al., "Cavitation-Enhanced Ultrasound Thermal Therapy by Combined Low- and High-Frequency Ultrasound Exposure," Ultrasound in Med. & Biol., vol. 32, No. 5, pp. 759-767 (2006).

(Continued)

*Primary Examiner* — Thomas Doughtery
(74) *Attorney, Agent, or Firm* — Muncy, Geissler, Olds & Lowe, P.C.

(57) ABSTRACT

A flexible ultrasound actuator is provided. The flexible ultrasound actuator includes a fixing element and a piezoelectric film structure. At least two ends of the piezoelectric film structure are fixed on the fixing element. The piezoelectric film structure comprises at least two curvatures.

15 Claims, 2 Drawing Sheets

(56) References Cited

U.S. PATENT DOCUMENTS

| | | | |
|---|---|---|---|
| 6,831,985 B2* | 12/2004 | Takei | 381/190 |
| 6,842,087 B2* | 1/2005 | Yamauchi | 333/187 |
| 6,958,255 B2 | 10/2005 | Khuri-Yakub et al. | |
| 7,486,004 B2 | 2/2009 | Allan et al. | |
| 2010/0246862 A1* | 9/2010 | Ihl et al. | 381/190 |
| 2011/0175488 A1* | 7/2011 | Shibata et al. | 310/319 |
| 2013/0208572 A1* | 8/2013 | Klee et al. | 367/180 |
| 2014/0167560 A1* | 6/2014 | Onda | 310/311 |

FOREIGN PATENT DOCUMENTS

| | | |
|---|---|---|
| TW | 480199 B | 3/2002 |
| TW | 200934271 | 8/2009 |
| TW | I325095 B | 5/2010 |

OTHER PUBLICATIONS

Toda, "Cylindrical PVDF Film Transmitters and Receivers for Air Ultrasound," IEEE Trans. On Ultrasonics, Ferroelectrics and Frequency Control, vol. 49, No. 5, pp. 626-634 (May 2002).

Ladabaum et al., "Surface Micromachined Capacitive Ultrasound Transducers," IEEE Trans. On Ultrasonics, Ferroelectrics and Frequency Control, vol. 45, No. 3, pp. 678-690 (May 1998).

Maione et al., "Transducer Design for a Portable Ultrasound Enhanced Transdermal Drug-Delivery System," IEEE Trans. On Ultrasonics, Ferroelectrics and Frequency Control, vol. 49, No. 10, pp. 1430-1436 (Oct. 2002).

Park et al., "Ultrasound Mediated Transdermal Insulin Delivery in Pigs Using Lightweight Transducer," Pharmaceutical Research, Research Paper, Springer Science+ Research, pp. 1-6 (2007).

* cited by examiner

FLEXIBLE ULTRASOUND ACTUATOR

This application claims the benefit of Taiwan application Serial No. 101140281, filed Oct. 31, 2012, the disclosure of which is incorporated by reference herein in its entirety.

TECHNICAL FIELD

The disclosed embodiments relate in general to an ultrasound actuator, and more particularly to a flexible ultrasound actuator.

DESCRIPTION OF THE RELATED ART

The research and development of the ultrasound wave is related to the producing and receiving the ultrasound wave in an article. In 1883, an ultrasound actuator is presented to the public. Afterwards, several mechanical ultrasound actuators with air whistle or liquid whistle are presented. Because the cost of those mechanical ultrasound actuators is low, they still widely used in the ultrasound wave technology.

In the early 20th century, electrical technology is developed. Some materials can be used for making ultrasound actuators according to the piezoelectic effect and the magnetostriction effect. In 1917, French physicist, Paul Langevin, used piezoelectric quartz to make a sandwich type ultrasound actuator, Langevin vibrator. It can be used to explore an undersea submarine. As the ultrasound is widely used in the military and the people's livelihood industries, a magnetostriction ultrasound actuator having high power, an electric type ultrasound actuator, an electromagnetic force type ultrasound actuator and an electrostatic type ultrasound actuator are presented.

Recently, it is found that the permeability of drugs of low frequency (20 kHz to 100 kHz) ultrasound wave is higher then that of 0.7 MHz ultrasound wave 1000 times. Similar studies are popular in Harvard University, Pennsylvania State University and Massachusetts. Moreover, according to the statement from FDA of USA, the sound intensity of the ultrasound wave should be controlled at 720 mW/cm2. Therefore, how to use a low frequency ultrasound wave to import drugs into the skin is a development target.

SUMMARY

The disclosure is directed to a flexible ultrasound actuator.

According to one embodiment, a flexible ultrasound actuator is provided. The flexible ultrasound actuator comprises a fixing element and a piezoelectric film structure. At least two ends of the piezoelectric film structure are fixed on the fixing element. The piezoelectric film structure comprises at least two curvatures.

Figure 1:
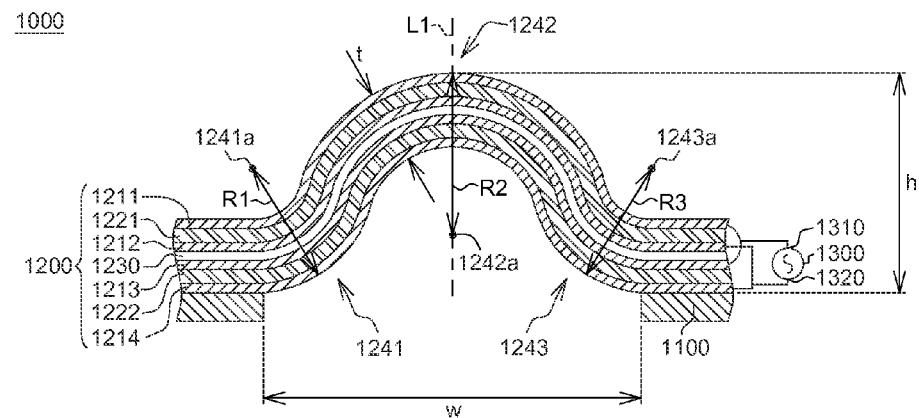
FIG. 1 is a flexible ultrasound actuator of a first embodiment.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

First Embodiment

Please referring to FIG. 1, a flexible ultrasound actuator 1000 of the first embodiment is shown. The flexible ultrasound actuator 1000 comprises a fixing element 1100, a piezoelectric film structure 1200 and a driving unit 1300. The fixing element 1100 is used for fixing varied elements. For example, the fixing element 1100 can be a carrying board or a frame. The piezoelectric film structure 1200 is used for producing an ultrasound wave. For example, the piezoelectric film structure 1200 can be formed by one, two or more than two piezoelectric layers. At least two ends of the piezoelectric film structure 1200 are fixed on the fixing element 1100. The portion which is not fixed can vibrate and produce the ultrasound wave. The driving unit 1300 is used for providing a driving signal. For example, the driving unit 1300 may be an alternating current power source. The driving unit 1300 is used for driving the piezoelectric film structure 1200 to vibrate for producing the ultrasound wave.

The piezoelectric film structure 1200 of the present embodiment has at least two curvatures. For example, the piezoelectric film structure 1200 has a first bending segment 1241, a second bending segment 1242 and a third bending segment 1243. The second bending segment 1242 is disposed between the first bending segment 1241 and the third bending segment 1243. The curvatures of the first bending segment 1241, the second bending segment 1242 and the third bending segment 1243 can be identical or different.

Regarding the relationship between the first bending segment 1241, the second bending segment 1242 and the third bending segment 1243, the first bending segment 1241 of the present embodiment and the third bending segment 1243 are symmetrical to a central line L1. The curvature (1/R1) of the first bending segment 1241 and the curvature (1/R3) of the third bending segment 1243 may be identical, such that the piezoelectric film structure 1200 may be vibrated stably.

In the present embodiment, the curvatures 1/R1) of the first bending segment 1241 and the curvature (1/R3) of the third bending segment 1243 can be larger than the curvature (1/R2) of the second bending segment 1242. Or, the curvature (1/R1) of the first bending segment 1241 and the curvature (1/R3) of the third bending segment 1243 can be smaller then the curvature (1/R2) of the second bending segment 1242. By adjusting the curvatures of the first bending segment 1241, the second bending segment 1242 and the third bending segment 1243, the frequency of the ultrasound wave of the piezoelectric film structure 1200 can be controlled. In the present embodiment, due to the suitable design, the piezoelectric film structure 1200 may produce the ultrasound wave having low frequency with 20 to 200 KHz.

Moreover, the bending direction of the first bending segment 1241, the second bending segment 1242 and the third bending segment 1243, the curvature centers 1241a, 1243a of the first bending segment 1241 and the third bending segment 1243 are located at one side, such as top side, of the piezoelectric film structure 1200, the curvature center of the second bending segment 1242 is located at another side, such as bottom side, of the piezoelectric film structure 1200.

Regarding the detail structure of the piezoelectric film structure 1200, the thickness t of the piezoelectric film structure 1200 is 10 to 500 μm, the height h of the piezoelectric film structure 1200 is 0.5 to 5 mm, and the width W of the piezoelectric film structure 1200 is 2 to 10 mm. The piezoelectric film structure 1200 comprises a first electrode layer 1211, a first piezoelectric layer 1221, a second electrode layer 1212, an adhesive layer 1230, a third electrode layer 1213, a second piezoelectric layer 1222 and a fourth electrode layer 1214. The material of the first piezoelectric layer 1221 and the second piezoelectric layer 1222 is polyvinylidenefluoride (PVDF) or a composite material thereof.

The first piezoelectric layer 1221 is disposed between the first electrode layer 1211 and the second electrode layer 1212. The first electrode layer 1211 and the second electrode layer 1212 are used for driving the first piezoelectric layer 1221. When the first piezoelectric layer 1221 is applied a varied electric field, the electric dipole moment is elongated according to the varied electric field, and the first piezoelectric layer 1221 will be elongated along the direction of the electric field. The mechanical deformation formed by the electric field is called as converse piezoelectric effect.

The adhesive layer 1230 is used for adhering the third electrode layer 1213 and the second electrode layer 1212. The second piezoelectric layer 1222 is disposed between the third electrode layer 1213 and the fourth electrode layer 1214. Similarly, the third electrode layer 1213 and the fourth electrode layer 1214 are used for driving the second piezoelectric layer 1222. The second piezoelectric layer 1222 will be mechanical deformed due to the converse piezoelectric effect.

The first electrode layer 1211, the first piezoelectric layer 1221, the second electrode layer 1212, the adhesive layer 1230, the third electrode layer 1213, the second piezoelectric layer 1222 and the fourth electrode layer 1214 are stacked in turn. When the piezoelectric film structure 1200 is driven to vibrate, the first electrode layer 1211, the first piezoelectric layer 1221, the second electrode layer 1212, the adhesive layer 1230, the third electrode layer 1213, the second piezoelectric layer 1222 and the fourth electrode layer 1214 will be mechanical deformed together.

In the present embodiment, the polarity of the first piezoelectric layer 1221 and the second piezoelectric layer 1222 are identical. The driving unit 1300 is an alternating current power source. The driving unit 1300 has a first electrode 1310 and a second electrode 1320. The first electrode 1310 and the second electrode 1320 are exchanged between the positive electrode and the negative electrode. The first electrode layer 1211 and the third electrode layer 1213 are electrically connected to the first electrode 1310. The second electrode layer 1212 and the fourth electrode layer 1214 are electrically connected to the second electrode 1320.

Under the relationship of connection, when the first piezoelectric layer 1221 and the second piezoelectric layer 1222 are driven, the first piezoelectric layer 1221 and the second piezoelectric layer 1222 may move towards the same direction, such that the piezoelectric film structure 1200 may produce the ultrasound wave.

Second Embodiment

Figure 2:
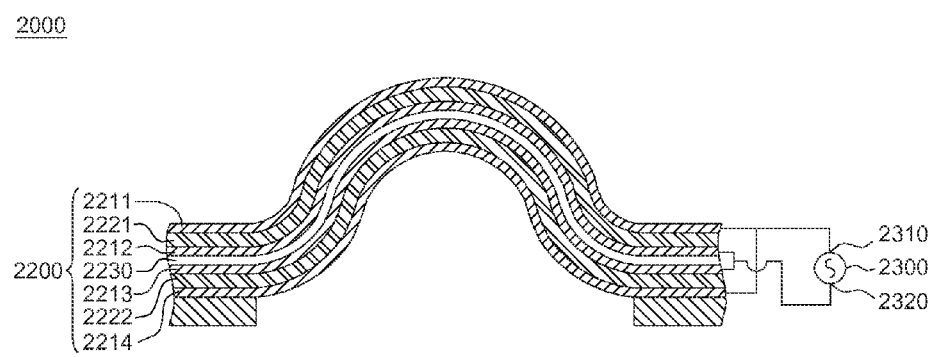
FIG. 2 is a flexible ultrasound actuator of a second embodiment.

Please referring to FIG. 2, a flexible ultrasound actuator 2000 of the second embodiment is shown. The flexible ultrasound actuator 2000 of the present embodiment and the flexible ultrasound actuator 1000 of the first embodiment are different in the polarity of the first piezoelectric layer 2221 and the second piezoelectric layer 2222 and the relationship of the connection between the piezoelectric film structure 2200 and the driving unit 2300, other similarity will not be repeated again.

As shown in FIG. 2, the polarity of the first piezoelectric layer 2221 and the second piezoelectric layer 2222 are contrary. The first electrode layer 2211 and the fourth electrode layer 2214 are electrically connected to the first electrode 2310, the second electrode layer 2212 and the third electrode layer 2213 are electrically connected to the second electrode 2320.

According to the relationship of connection, when the first piezoelectric layer 2221 and the second piezoelectric layer 2222 are driven, the first piezoelectric layer 2221 and the second piezoelectric layer 2222 may move along the same direction, such that the piezoelectric film structure 1200 may produce the ultrasound wave.

Third Embodiment

Figure 3:
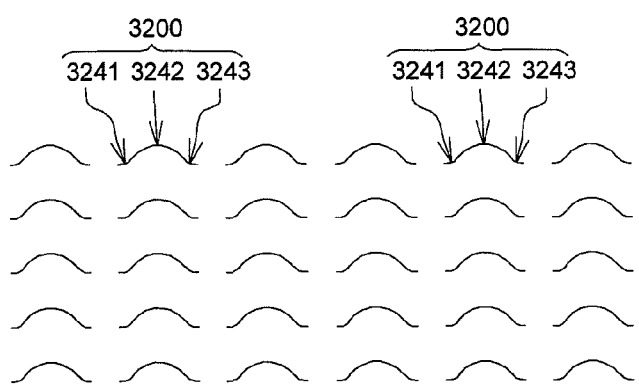
FIG. 3 is a flexible ultrasound actuator of a third embodiment.

Please referring to FIG. 3, a flexible ultrasound actuator 3000 of the third embodiment is shown. The flexible ultrasound actuator 3000 of the present embodiment and the flexible ultrasound actuator 1000 of the first embodiment are different in the quality of the first bending segment 3241, the second bending segment 3242 and the third bending segment 3243, other similarity will not be repeated again.

As shown in FIG. 3, the piezoelectric film structure 3200 has several first bending segments 3241, several second bending segments 3242 and several third bending segments 3243. The first bending segments 3241, the second bending segments 3242 and the third bending segments 3243 are arranged in a matrix.

In the present embodiment, the curvatures of all of the first bending segments 3241 may be identical, the curvatures of all of the second bending segments 3242 may be identical, the curvatures of all of the third bending segments 3243 may be identical. Therefore, when the piezoelectric film structure 3200 is driven, an uniform ultrasound wave may be produced.

Because the first bending segments 3241, the second bending segments 3242 and the third bending segments 3243 are connected with each other to form the piezoelectric film structure 3200, the piezoelectric film structure 3200 can be bended arbitrarily. Therefore, the flexible ultrasound actuator 3000 may closely contact the skin of human to import drugs into the skin.

Fourth Embodiment

Figure 4:
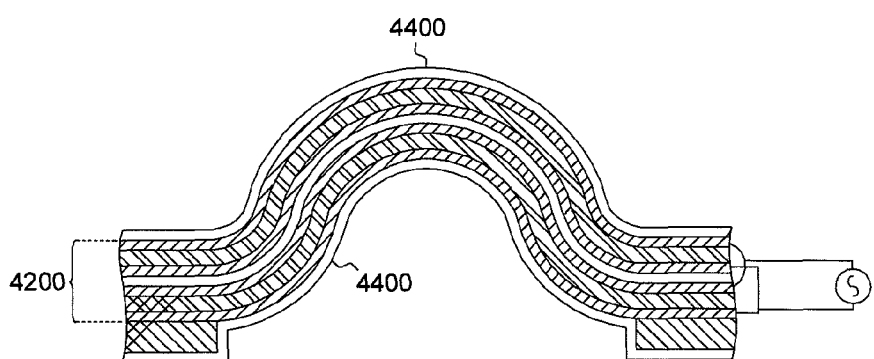
FIG. 4 is a flexible ultrasound actuator of a fourth embodiment.

Please referring to FIG. 4, a flexible ultrasound actuator 4000 of the fourth embodiment is shown. The flexible ultrasound actuator 4000 of the present embodiment and the flexible ultrasound actuator 1000 of the first embodiment are different in that the flexible ultrasound actuator 4000 further comprises a waterproofing film 4400, other similarity will not be repeated again.

The waterproofing film 4400 may at least cover the piezoelectric film structure 4200 for preventing the piezoelectric film structure 4200 from leaking current, getting wet or getting pollution. The waterproofing film 4400 may also cover the fixing element. Therefore, the reliability of the piezoelectric film structure 4200 can be improved.

In FIG. 4, the piezoelectric film structure 4200 is similar to the piezoelectric film structure 1200 of FIG. 1. In one embodiment, the waterproofing film 4400 may be applied on the piezoelectric film structure 2200 of FIG. 2; wherein the first electrode layer 2211 and the fourth electrode layer 2214 are electrically connected to the first electrode 2310, and the second electrode layer 2212 and the third electrode layer 2213 are electrically connected to the second electrode 2320.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A flexible ultrasound actuator, comprising:
a fixing element; and
a piezoelectric film structure, wherein at least two ends of the piezoelectric film structure are fixed on the fixing element, and the piezoelectric film structure comprises at least two curvatures;
wherein the piezoelectric film structure has at least one first bending segment, at least one second bending segment, and at least one third bending segment, and the second bending segment is disposed between he first bending segment and the third bending segment;
wherein a curvature of the first bending segment and a curvature of the third bending segment are identical and the curvature of the first bending, segment is larger or smaller than a curvature of the second segment.

2. The flexible ultrasound actuator according to claim 1, wherein the piezoelectric film structure comprises:
a first electrode layer;
a first piezoelectric layer;
a second electrode layer, wherein the first piezoelectric layer is disposed between the first electrode layer and the second electrode layer;
an adhesive layer;
a third electrode layer, wherein the adhesive layer is used for adhering the third electrode layer and the second electrode layer;
a second piezoelectric layer; and
a fourth electrode layer, wherein the second piezoelectric layer is disposed between the third electrode layer and the fourth electrode layer.

3. The flexible ultrasound actuator according to claim 2, wherein a polarity of the first piezoelectric layer and the second piezoelectric layer are identical.

4. The flexible ultrasound actuator according to claim 3, further comprising:
a driving unit, for driving the piezoelectric film structure to vibrate for producing an ultrasound wave;
wherein the driving unit is an alternating current power source, the driving unit has a first electrode and a second electrode, the first electrode layer and the third electrode layer are electrically connected to the first electrode, and the second electrode layer and the fourth electrode layer are electrically connected to the second electrode.

5. The flexible ultrasound actuator according to claim 2, wherein a polarity of the first piezoelectric layer and the second piezoelectric layer are contrary.

6. The flexible ultrasound actuator according to claim 5, further comprising:
a driving unit, for driving the piezoelectric film structure to vibrate for producing an ultrasound wave;
wherein the driving unit is an alternating current power source, the driving unit has a first electrode and a second electrode, the first electrode layer and the fourth electrode layer are electrically connected to the first electrode, and the second electrode layer and the third electrode layer are electrically connected to the second electrode.

7. The flexible ultrasound actuator according to claim 2, wherein a material of the first piezoelectric layer and the second piezoelectric layer is polyvinylidenefluoride (PVDF) or a composite material thereof.

8. The flexible ultrasound actuator according to claim 1, further comprising:
a waterproofing film, covering the piezoelectric film structure.

9. The flexible ultrasound actuator according to claim 1, wherein the first bending segment and the third bending segment are symmetrical to a central line.

10. The flexible ultrasound actuator according to claim 1, wherein curvature centers of the first bending segment and the third bending segment are located at one side of the piezoelectric film structure, and another curvature center of the second bending segment is located at another side of the piezoelectric film structure.

11. The flexible ultrasound actuator according to claim 1, wherein a quantity of the at least one first bending segment is plural, a quantity of the at least one second bending segment is plural, and a quantity of the at least one third bending segment is plural.

12. The flexible ultrasound actuator according to claim 11, wherein the first bending segments, the second bending segments and the third bending segments are arranged in a matrix.

13. The flexible ultrasound actuator according to claim 1, wherein a thickness of the piezoelectric film structure is 10 to 500 μm.

14. The flexible ultrasound actuator according to claim 1, wherein a height of the piezoelectric film structure is 0.5 to 5 mm.

15. The flexible ultrasound actuator according to claim 1, wherein a width of the piezoelectric film structure is 2 to 10 mm.

* * * * *